United States Patent [19]

Hou et al.

[11] Patent Number: 4,992,591
[45] Date of Patent: Feb. 12, 1991

[54] PREPARATION OF ALPHA-(3,4-DISUBSTITUTED ARYL) CYCLIC KETONES

[75] Inventors: Donald Hou, Verona; Janet L. Mas, Scotch Plains, both of N.J.

[73] Assignee: Schering Corporation, Kenilworth, N.J.

[21] Appl. No.: 454,670

[22] Filed: Dec. 21, 1989

[51] Int. Cl.⁵ .............................................. C07C 45/67
[52] U.S. Cl. .................................... 568/315; 568/316
[58] Field of Search .............................. 568/316, 315

[56] References Cited

FOREIGN PATENT DOCUMENTS 47-47376 11/1972 Japan ................................ 568/316

OTHER PUBLICATIONS

M. Kosugi et al., Chem. Letters, pp. 939–940 (1982).

*Primary Examiner*—James H. Reamer
*Attorney, Agent, or Firm*—Edward H. Mazer; James R. Nelson; Stephen I. Miller

[57] ABSTRACT

A method for producing a compound of the formula

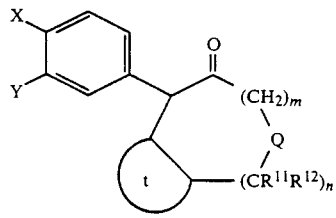

wherein:
- $R^1$, $R^{11}$ and $R^{12}$ may be the same or different and each is hydrogen or alkyl;
- Q is methylene, —O— or —S—;
- m and n are independently variable and may each have a value of 0, 1 or 2;
- X is hydrogen, halo, alkyl, alkylthio, alkylsulfinyl, alkylsulfonyl, hydroxy, alkoxy or trifluoromethyl;
- Y is hydrogen, hydroxy, alkoxy,

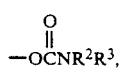

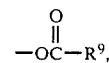

—N(R¹)₂,

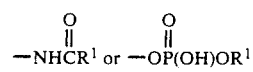

where $R^1$ is as defined above;
ring t represents a fused thiophene or fused benzene ring, said fused benzene ring optionally being substituted with a substituent Z as defined below; and
Z is X as defined above, amino, alkylamino or

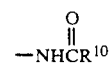

{wherein $R^{10}$ is hydrogen, alkyl or aryl}, comprising reacting a compound of formula II or formula III

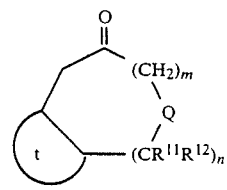

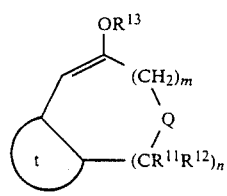

with a compound of the formula

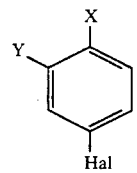

where Hal is a halogen; and
$R^{13}$ is acetyl, or $Si(R^{14})_3$ where each $R^{14}$ independently is alkyl or aryl is disclosed.

17 Claims, No Drawings

PREPARATION OF ALPHA-(3,4-DISUBSTITUTED ARYL) CYCLIC KETONES

BACKGROUND OF THE INVENTION

The present invention is directed at an improved method for producing α-(3,4-disubstituted aryl) cyclic ketones. More specifically, the present invention is directed at a method for preparing (±) - (1R,S)-1-(4-chloro-3-methoxyphenyl)-3,4-dihydro-2(1H)-naphthalenone.

A method for producing this compound has been disclosed in European Patent Publication No. 0 230 270, which is directed at fused benzazepines useful in the treatment of psychoses, pain and/or depression. This publication discloses α-(3,4-disubstituted aryl) cyclic ketones as intermediate XVIII and also discloses a method for producing same. This publication discloses that intermediate XVIII can be prepared by first reacting a 3,4-disubstituted 1-(magnesium halide) phenyl with aryl ketones. The resulting compound is dehydrated using acid catalysts with continuous removal of water. The dehydrated compound then may be converted to a compound of formula XVIII by the sequential use, for example, of m-chloroperbenzoic acid, an alkali metal hydroxide, and then a strong mineral acid. Formula I of the present invention includes the compound of formula XVIII of this publication.

While the process disclosed above produces the desired compounds, the process has the disadvantage of being a multi-step process that proceeds in moderate overall yields.

M. Kosugi, et. al. in J. Chemical Society, Chemical Communications page 344 (1983) and references cited therein disclose a method for α-phenylation of ketones utilizing a palladium catalyst system and stannyl enolates generated "in situ" from enol acetates and tri-n-butyltin methoxide.

M. A. Cuifolini in J. Organic Chemistry, Volume 53, page 4149 (1988) discloses palladium-catalyzed displacement of halide from aromatic substrates by "soft" enolates (pKa<15). This publication describes the formation of benzo-fused five-or-six-membered rings via intramolecular cyclizations.

I. Kuwajima, et. al. in J. Am. Chem. Soc., Volume 104, page 6831 (1982) disclose a method for palladium catalyzed α-phenylation of α-stannyl ketones generated "in situ" from silyl enol ethers and tri-n-butyl tin fluoride. However, each of these three publications utilizes different substrates than those of the presently desired compounds, i.e. the aromatic and ketone portions of the substrates of the subject compounds differ from these publications.

Accordingly, an object of the present invention is a less costly method for producing the compounds of formula I below.

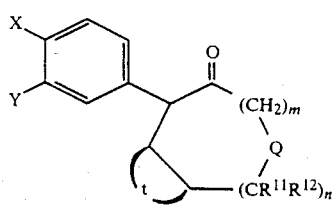

SUMMARY OF THE INVENTION

This invention discloses a method for producing a compound of the formula.

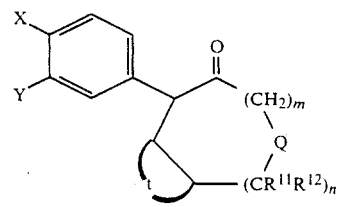

wherein:

$R^1$, $R^{11}$ and $R^{12}$ may be the same or different and each is hydrogen or alkyl;

Q is methylene, —O— or —S—;

m and n are independently variable and may each have a value of 0, 1 or 2;

X is hydrogen, halo, alkyl, alkylthio, alkylsulfinyl, alkylsulfonyl, hydroxy, alkoxy or trifluoromethyl;

Y is hydrogen, hydroxy, alkoxy,

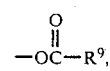

-N(R$^1$)$_2$,

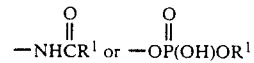

where $R^1$ is as defined above; ring t represents a fused thiophene or fused benzene ring, fused benzene ring optionally being substituted with a substituent Z as defined below;

$R^2$ and $R^3$ are independently hydrogen, alkyl, aralkyl, cycloalkyl, aryl, hydroxyalkyl, or alkoxyalkyl;

in addition, when one of $R^2$ and $R^3$ is as defined above, the other may be —R$^4$NR$^5$R$^6$ {wherein R$^4$ is alkanediyl, R$^5$ is hydrogen or alkyl and R$^6$ is alkyl or R$^5$ and R$^6$ together with the nitrogen atom form a 1-azetidinyl, 1-pyrrolidinyl, 1-piperidinyl, 1-(4-alkylpiperazinyl), 4-morpholinyl or 1-(hexahydroazepinyl) group};

in further addition, R$^2$ and R$^3$ together with the nitrogen atom may form a 1-azetidinyl, 1-pyrrolidinyl, 1-piperidinyl, 4-morpholinyl, 1-(4-alkylpiperazinyl), 1-(4-alkoxyalkylpiperazinyl), 1-(4-hydroxyalkylpiperazinyl), 1-(3-hydroxyazetidinyl), 1-(3-alkoxyazetidinyl), 1-(3-hydroxypyrrolidinyl), 1-(3-alkoxypyrrolidinyl), 1-(3- or 4-hydroxypiperidinyl), 1-(3- or 4-alkoxypiperidinyl), 1-(4-oxopiperidinyl) or 1-(3-oxopyrrolidinyl) ring;

in still further addition, when R$^2$ is hydrogen, R$^3$ may be —CHR$^7$CO$_2$R$^8$, wherein R$^7$ and R$^8$ are independently hydrogen, alkyl or aralkyl;

R$^9$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, cycloalkoxyalkyl, alkoxy, aralkoxy, cycloalkoxy, aryloxy or —CHR$^7$NHR$^8$ {wherein R$^7$ and R$^8$ are as defined above}; and Z is X as defined above, amino, alkylamino or

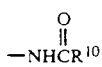

{wherein $R^{10}$ is hydrogen, alkyl or aryl} comprising reacting a compound of the formula II or III:

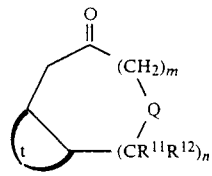

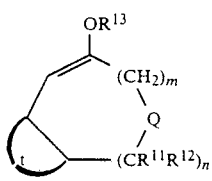

with a compound of the formula

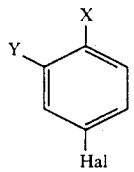

wherein Hal is a halogen;

$R^{13}$ is acetyl, or $Si(R^{14})_3$ where each $R^{14}$ independently is alkyl or aryl with suitable hydroxy and amino protecting groups utilized where necessary.

The reaction preferably is catalyzed by an organo transition metal, such as nickel or palladium, preferably a palladium complex. Preferably, X and Hal are not both bromine.

In preferred embodiments of the present invention:
ring t is a fused benzene;
Q is —CH$_2$—;
m is zero;
n is 1;
$R^{11}$ and $R^{12}$ are H;
X is halogen, particularly chlorine;
Y is methoxy; and
Hal is halogen, particularly bromine.

When $R^{13}$ is an acetyl a preferred catalyst system comprises:

Pd(OAc)$_2$ and (o-tolyl)$_3$P; (n-Bu)$_3$SnOMe is used to generate the stannyl enolate "in situ". Toluene is the preferred solvent, and the preferred reaction temperature is 105°-110° C.

When Si(R$^{14}$)$_3$ represents
Si(Me)$_3$ or
Si(tBu)Me$_2$, the catalyst system preferably comprises PdCl$_2$[(o-tolyl)$_3$P]$_2$; (n-Bu)$_4$NF is preferred for generating the enolate. The preferred solvent is DMF and the preferred reaction temperature is 80°-100° C.

With compound II, the catalyst system preferably comprises:
Pd(OAc)$_2$ and (o-tolyl)$_3$P; NaH is the preferred base to generate the enolate at 0°-25° C. The preferred solvent is DMF, and the preferred reaction temperature is 100°-135° C.

DETAILED DESCRIPTION OF THE INVENTION

When utilized herein and in the appended claims, the following terms, unless otherwise specified, have the following scope:

halo-represents fluoro, chloro, bromo or iodo;

alkyl (including, for example, the alkyl portions of alkylthio, alkoxy, aralkyl, alkoxyalkoxy, etc.) - represents straight or branched carbon chains having 1 to 6 carbon atoms;

cycloalkyl groups (including the cycloalkyl portion in cycloalkoxy groups) - represents saturated carbocyclic rings having 3 to 7 carbon atoms;

alkanediyl - represents a divalent, straight or branched hydrocarbon chain having from 1 to 6 carbon atoms, the two available bonds being from the same or different carbon atoms thereof, e.g., methylene, ethylene, ethylidene, —CH$_2$CH$_2$CH$_2$—, —CH$_2$CHCH$_3$, —CHCH$_2$CH$_3$, etc.; and aryl (including, for example, the aryl moiety in aralkyl or aralkoxy groups) - represents unsubstituted phenyl and phenyl mono substituted by alkyl, hydroxy, alkoxy, halo or trifluoromethyl.

As used herein "hydroxy protecting group" and "amino protecting group" mean any groups conventionally used for these purposes, with the only requirements being compatibility during protection and deprotection reactions with conventional reagents for this purpose which will not adversely affect the structure of the compounds. Typical of such groups are those listed in Green, "Protecting Groups in Organic Synthesis" John Wiley and Sons, New York, NY (1981). Examples of "hydroxy protecting groups" are ethers such as methyl, methoxymethyl, methylthiomethyl, 2-methoxyethoxymethyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, 2-(phenylselenyl)ethyl, t-butyl, allyl, benzyl, triphenylmethyl, alpha naphthyldiphenylmethyl, paramethoxyphenyldiphenylmethyl, trimethylsilyl, isoamyldimethylsilyl, isopropyldimethylsilyl, t-butyldimethylsilyl, t-butyldiphenylsilyl, tribenzylsilyl, and triisopropylsilyl, as well as esters such as adamantoate, 2,4,5-trimethylbenzoate, N-phenylcarbamate and the like. Examples of "amino protecting groups" are carbamates such as methyl, 2-trimethylsilylethyl, 1,1-dimethylpropynyl, 1-methyl-1-phenylethyl, 1-methyl-1-(4-biphenylyl)ether, t-butyl, cyclobutyl, 1-methylcyclobutyl, 1-adamantyl, vinyl, cinnamyl, 8-quinolyl, benzyl and 9-anthrylmethyl, amides such as N-acetyl, N-picolinoyl, N-benzoyl and N-phthaloyl as well as special protecting groups such as N-allyl, N-methoxymethyl, N-benzyloxymethyl, N-tetrahydropyranyl, N-benzyl, N-o-nitrobenzyl, N-triphenylmethyl, N-(p-methoxyphenyl)diphenylmethyl, N-benzylidene, N-p-nitrobenzylidene, N-diphenylphosphinyl, N-2,4,6-trimethylbenzenesulfonyl, N-toluenesulfonyl and the like.

A "suitable inert organic solvent" can be any organic solvent or combination of solvents that is unreactive in the reaction being conducted and is a solvent for the reactants. Typical solvents include tetrahydrofuran (THF), dimethylformamide, dimethylsulfoxide, and toluene.

The term "enolate generator" can be any organic or inorganic base that will generate the enolate of compounds of formula II. Examples of organic base enolate generators include the alkylamines such as triethylamine, 1,8-diazabicylo[5.4.0]unde-7-ene, diethylisopropylamine and lithium diisopropylamide. Examples of inorganic base enolate generators include NaH, KH, LiH and KOtBu.

The reactions are carried out neat or in suitable inert organic solvent, e.g., toluene, DMF or DMSO at temperatures ranging from 0° C →135° C. When a compound of formula II is used, an organic or inorganic base, e.g., TEA, NaH, KH, or KOtBu may be used to generate the enolate; and with compounds of formula III, $(R^{15})_3$SnOMe or $(R^{16})_4$NF are used to generate the enolate wherein each $R^{15}$ and $R^{16}$ independently is alkyl or aryl.

The catalyst system is comprised of an organo transition metal complex, preferably either a nickel or palladium complex with either phosphine or phosphite ligands. These ligands may be various alkyl- or arylphosphines or alkyl-or arylphosphites such as $PPh_3$, P(o-tolyl)$_3$, P(m-tolyl)$_3$, P(p-tolyl)$_3$, (2-furyl)$_3$P, P(OEt)$_3$, P(OPh)$_3$, P(O-o-tolyl)$_3$ as well as bidendate ligands such as 1,2-bis(diphenylphosphino)ethane, (R)-(+)-2,2,bis (diphenylphosphino)propane, (R)-(+)-2,2'-bis (diphenylphosphino)-1,1'-binaphthyl and the like.

Also R, $R^1$, $R^{11}$, $R^{12}$, X, Y and Z groups in formula I may be varied by appropriate selection of starting materials from which the compounds are synthesized or by reacting a compound of formula I with a suitable reagent to effect the desired conversion of the substituent to another R, $R^1$, $R^{11}$, $R^{12}$, X, Y and Z group. The latter procedure is particularly applicable for changing the substituents X. For example, a chlorine substituent may be added in place of hydrogen by reaction with a chlorinating agent such as sulfuryl chloride in a non-reactive solvent A hydroxymethyl substituent in the X position may be added in place of hydrogen by reaction with formaldehyde in a suitable solvent system, e.g., in a mixed solvent system consisting of dimethoxyethane and aqueous potassium hydroxide, preferably at an elevated temperature. Such a hydroxymethyl substituent may be reduced to an X methyl group by reaction with a catalyst such as palladium hydroxide in a hydrogen atmosphere under pressure. Methoxy substituents may be converted to hydroxy, e.g., by refluxing in a mixture of sodium hydride, DMF and ethanethiol, or by reaction with concentrated hydrobromic acid. Other substitutions may be accomplished using standard techniques. In the case where there is a hydroxy or amino group that may interfere with the reaction, these groups may be protected with either a "hydroxy protecting group" or an "amino protecting group".

Examples I–IV below disclose methods for the preparation of (±)-(1R,S)-1-(4-chloro-3-methoxyphenyl)3,4-dihydro-2(1H)-naphthalenone.

EXAMPLE I

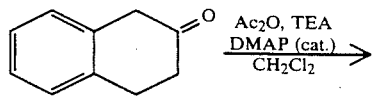

β-tetralone
16

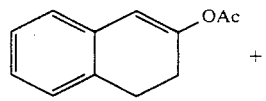

17

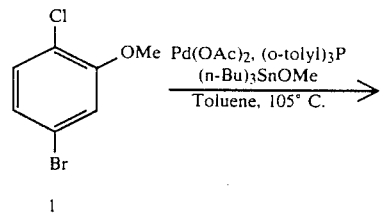

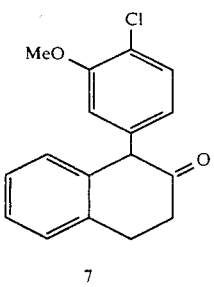

7

(A) PREPARATION OF
2-acetoxy-3,4-dihydronaphthalene

Charge a nitrogen-flushed 12-L round bottomed flask equipped with a mechanical stirrer and reflux condenser with β-tetralone (1,308.0 grams, 8.947 moles), triethylamine (1,089.0 grams, 10.763 moles), acetic anhydride (1,104.0 grams, 10.810 moles) and 1 L methylene chloride. Cool in an ice/water bath and add 4-dimethylamino pyridine (55.03 grams, 0.4501 moles) portionwise over a 10 minute period (slight exotherm noted). Stir for 23 hours at RT and then add 1 L methylene chloride, wash with 1×2 L 5% HCl solution, 1×1 L water, 1×1 L saturated sodium bicarbonate solution, 1×1 L saturated salt solution, dry over magnesium sulfate, concentrate on a Büchi rotavapor and distill (118°–123° C, 1 Torr) to obtain pure product.

$^1$H NMR: (CDCl$_3$), δ=6.9–7.20 (m,4 H); 6.21 (s, 1 H); 2.97 (t, 2H, J=7.0 Hz); 2.52 (t, 2H, J=7.0 Hz); 2.18 (s, 3H).

(B) PREPARATION OF
(±)-(1RS)-1-(4-Chloro-3-methoxyphenyl)-3,4-dihydro-2(1H)-naphthalenone (7)

Charge an oven dried, argon flushed 3-L 3-necked round bottomed flask equipped with a mechanical stirrer and reflux condenser with 2-acetoxy-3,4-dihydronaphthalene (100.69 grams, 0.5349 moles), 4-bromo-2-methoxy-1-chlorobenzene (116.81 grams, 0.5274 moles), palladium acetate (1.19 grams, 0.0053 moles), tri (o-tolyl)phosphine (3.24 grams, 0.0107 moles), tri-n-butyltin methoxide (172.83 grams, 0.5383 moles) and 1 L toluene. Place in an oil bath pre-heated to 100°–105° C for 20 hours. Distill off about 750 mL toluene, cool to RT, add 500 mL 5% HCl and 250 mL ethyl acetate, stir for a few minutes, filter through a pad of celite and wash the celite pad with 5×250 mL ethyl acetate. Separate the layers, extract the aqueous layer with 1×250 mL ethyl acetate, wash the combined organic layers with saturated sodium bicarbonate solution followed by saturated salt solution, dry over magnesium sulfate and concentrate on a Büchi rotavapor. Kugelrohr treat the resulting oil (heated to about 130° C., 1 Torr) to remove the more volatile by-products to yield product. An analytical sample can be prepared by flash chromatography (5–30% ethyl acetate/hexanes) followed by recrystallization (ethyl acetate/hexanes).

$^1$H NMR: (CDCl$_3$), δ=7.23–7.30 (m,4 H); 7.00 (d, 1 H J=7.0 Hz); 6.76 (d, 1H, J=1.9 Hz); 6.53 (dd, 1H, J=1.8, 8.0 Hz) 4.72 (s, 1H), 3.83 (s, 3H); 3.00–3.20 (m, 2H); 2.55–2.68 (m, 2H). mp 77°–78.5° C.

EXAMPLE II

PREPARATION OF (±)-(1RS)-1-(4-Chloro-3-methoxyphenyl)-3,4-dihydro-2(1H)-naphthalenone (7)

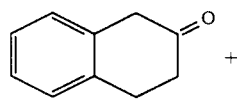

+

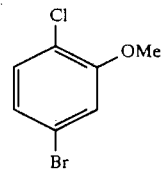

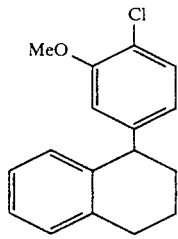

Charge an oven dried, argon flushed 25-mL two-necked round bottomed flask equipped with a stirring bar with β-tetralone (1.3095 grams, 8.9575 mmoles) and 5 mL dry dimethylformamide. Cool to 0° C with an ice bath, add sodium hydride (0.4299 grams, 8.9575 mmoles, 50% oil dispersion) and stir for 25 minutes. Filter the solution through a 5 mL syringe equipped with a bed of celite (dried in an oven) via a double-ended needle into an oven dried, argon flushed 25-mL round bottomed flask equipped with a stirring bar and reflux condenser which had been charged with 4-bromo-2-methoxy-1-chlorobenzene (1.5871 grams, 7.166 mmoles), palladium acetate (0.0079 grams 0.0350 mmoles) and tri(o-tolyl)phosphine (0.0213 grams, 0.070 mmoles). Heat at about 125° C (oil bath) for 21 hours, cool to RT and add ethyl acetate and 2N HCl. Separate the layers, extract the aqueous layers with two portions of ethyl acetate, wash the combined organic layers with saturated sodium bicarbonate solution followed by saturated salt solution, dry over magnesium sulfate and concentrate using a Büchi rotavapor to produce the named product.

EXAMPLE III

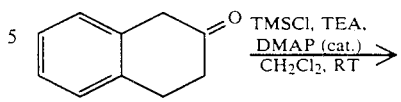

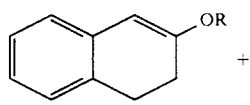

+

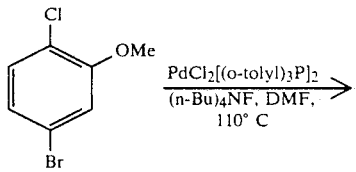

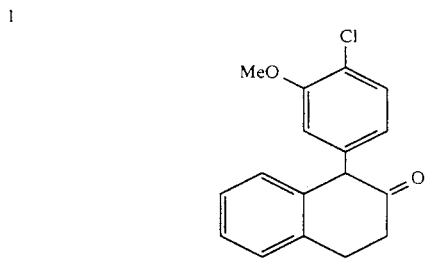

(A) PREPARATION OF 2-Trimethylsilyloxy-3,4-dihydronaphthalene (18)

Charge an oven dried, nitrogen flushed 100-mL round bottomed flask equipped with a stirring bar with β-tetralone (4.977 grams, 0.0340 moles), triethylamine (6.970 grams, 0.0689 moles), 4-dimethylamino pyridine (0.219 grams,0.0018 moles), trimethylsilyl chloride (7.704 grams, 0.0709 moles) and 30 mL methylene chloride. Stir at RT for 20 hours, filter, wash the solid with 1×20 mL methylene chloride, wash the combined organic layers with 1×5 mL saturated sodium bicarbonate solution, 1×5 mL water, dry over magnesium sulfate, concentrate on a Büchi rotavapor and distill (96°–99° C, 1 Torr) to yield the product as a viscous oil.

$^1$H NMR: (CDCl$_3$), δ=6.90–7.16 (m,4 H); 5.71 (s, 1 H); 2.90 (t, 2H, J=7.0 Hz); 2.38 (t,2H, J=7.0 Hz); 0.28 (s, 9H).

(B) PREPARATION OF (±)-(1RS)-1-(4-chloro-3-methoxyphenyl)-3,4-dihydro-2(1H)naphthalenone Charge an oven dried, argon flushed 25-mL 2-necked round bottomed flask equipped with a stirring bar and reflux condenser with 2-trimethylsilyloxy-3,4-dihydronaphthalene (0.4247 grams, 1.9449 mmoles) and tetra-n-butylammonium fluoride (2.3 mL, 2.30 mmoles, 1 M in tetrahydrofuran), stir for a few minutes and then add 4-bromo-2-methoxy-1-chlorobenzene (0.4336 grams, 1.9577 mmoles) dichlorobis(tri-o-tolyl-phosphine)palladium (0.0154 grams, 0.0196 mmoles) and 5 mL dimethylformamide. Heat the reaction mixture for 18 hours (oil bath temperature about 90° C ), cool to RT and add 5 mL water and 10 mL t-butylmethyl ether. Separate the layers, extract the aqueous layers with 3×5 mL t-butylmethyl ether, wash the combined organic layers with water and saturated salt solution, dry over magnesium sulfate and concentrate using a Büchi rotavapor to yield the final product.

EXAMPLE IV

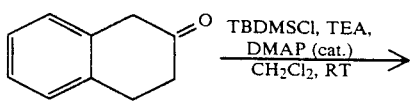

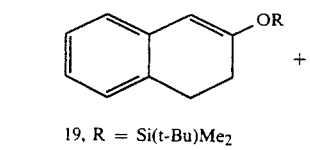

19, R = Si(t-Bu)Me₂

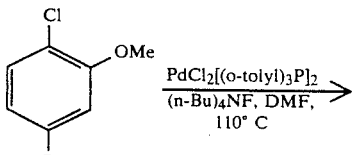

1

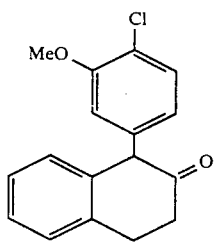

7

(A) PREPARATION OF
2-t-Butyldimethylsilyloxy-3,4-dihydronaphthalene (19)

Charge an oven dried, nitrogen flushed 125-mL round bottomed flask equipped with a stirring bar with β-tetralone (4.977 grams, 0.0340 moles), triethylamine (6.970 grams, 0.0689 moles), 4-dimethylamino pyridine (0.217 grams, 0.0018 moles), t-butyldimethylsilyl chloride (10.701 grams, 0.0709 moles) and 40 mL methylene chloride. Stir for 72 hours, filter, wash the filtrate with 1×5 mL saturated sodium bicarbonate solution, 1×5 mL water, dry over magnesium sulfate, concentrate using a Büchi rotavapor and distill (142°–145° C, 1 Torr) to obtain the named compound ¹H NMR (CDCl₃), δ=6.86–7.16 (m,4 H); 5.7 (s, 1 H); 2.90 (t, 2H, J=7.0 Hz); 2.36 (t, 3H, J=7.0 Hz); 0.94 (s, 9H); 0.22 (s, 6H).

(B) PREPARATION OF
(+)-(1RS)-1-(4-chloro-3-methoxyphenyl)-3,4-dihydro-2(1H)-naphthalenone Charge an oven dried, argon flushed 25-mL 2-necked round bottomed flask equipped with a stirring bar and reflux condenser with 2-t-butyldimethylsilyloxy-3,4-dihydronaphthalene (0.5007 grams, 1.9224 mmoles) and tetra-n-butylammonium fluoride (2.3 mL, 2.30 mmoles, 1 M in tetrahydrofuran), stir for a few minutes and then add 4-bromo-2-methoxy-2-chlorobenzene (0.4287 grams, 1.9356 mmoles), dichlorobis(tri-o-tolyl-phosphine)palladium (0.0154 grams, 0.0196 mmoles) and 5 mL dimethylformamide. Heat the reaction mixture for 18 hours (oil bath temperature about 90° C), cool to RT and add 5 mL water and 10 mL t-butylmethyl ether. Separate the layers, extract the aqueous layers with 3×5 mL t-butylmethyl ether, wash the combined organic layers with water and saturated salt solution, dry over magnesium sulfate and concentrate using a Büchi rotavapor to yield the product.

We claim:
1. A method for producing a compound of the formula

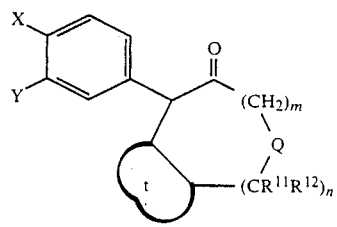

I wherein:
R¹, R¹¹ and R¹² may be the same or different and each is hydrogen or alkyl;
Q is methylene, —O— or —S—;
m and n are independently variable and may each have a value of 0, 1 or 2;
X is hydrogen, halo, alkyl, alkylthio, alkylsulfinyl, alkylsufonyl, hydroxy, alkoxy or trifluoromethyl;
Y is hydrogen, hydroxy, alkoxy

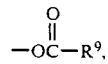

—N(R¹)₂,

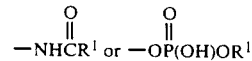

where R¹ is as defined above;
ring t represents a fused thiophen or fused benzene ring, said fused benzene ring optionally being substituted with a substituent Z as defined below;
R² and R³ are independently hydrogen, alkyl, aralkyl, cycloalkyl, aryl, hydroxyalkyl, or alkoxyalkyl;
in addition, when one of R² and R³ is as defined above, the other may be —R⁴NR⁵NR⁵R⁶ {wherein R⁴ is alkanediyl, R⁵ is hydrogen or alkyl and R⁶ is alkyl, or R⁵ and R⁶ together with the nitrogen atom form a 1-azetidinyl, 1-pyrrolidinyl, 1-piperidinyl, 1-(4-alkylpiperazinyl), 4-morpholinyl or 1-(hexahydroazepinyl) group};
in further addition, R² and R³ together with the nitrogen atom may form a 1-azetidinyl, 1-pyrrolidinyl, 1-piperidinyl, 4-morpholinyl, 1-(4-alkylpiperazinyl), 1-(4-alkoxyalkylpiperazinyl), 1-(4-hydroxyalkylpiperazinyl), 1-(3-hydroxyazetidinyl), 1-(3- aloxyazetidinyl), 1-(3-hydroxypyrrolidinyl), 1-(3-alkoxypyrrolidinyl), 1-(3- or 4-hydroxypiperidinyl), 1-(3- or 4-alkoxypiperidinyl), 1-(4-oxopiperidinyl) or 1-(3-oxopyrrolidinyl) ring;

in still further addition, when $R^2$ is hydrogen, $R^3$ may be $-CHR^7CO_2R^8$, wherein $R^7$ and $R^8$ are independently hydrogen, alkyl or aralkyl;

$R^9$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, cycloalkoxyalkyl, alkoxy, aralkoxy, cycloalkoxy, aryloxy or $-CHR^7NHR^8$ {wherein $R^7$ and $R^8$ are as defined above}; and Z is X as defined above, amino, alkylamino or

{wherein $R^{10}$ is hydrogen, alkyl or aryl} comprising reacting a compound of the formula II or formula III:

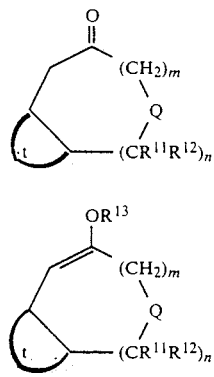

with a compound of the formula:

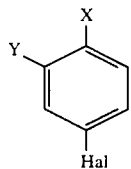

in the presence of a nickel transition metal catalyst or a palladium transition metal catalyst
where Hal is a halogen; and
$R^{13}$ is acetyl, or $Si(R^{14})_3$ where each $R^{14}$ independently is alkyl or aryl
with suitable hydroxy and amino protecting groups utilized where necessary.

2. The process of claim 1 wherein:
ring t is a fused benzene;
Q is $-CH_2-$;
m is zero;
n is 1; and
$R^{11}$ and $R^{12}$ are H.

3. The process of claim 1 wherein:
X is chlorine;
Y is methoxy; and
Hal is bromine.

4. The process of claim 1 wherein the catalyst comprises a nickel or palladium complex with alkyl- or aryl-phosphine or alkyl- or aryl-phosphite ligands.

5. The process of claim 1 wherein the catalyst is a palladium complex.

6. The process of claim 5 wherein the reactant comprises a compound of formula III.

7. The process of claim 6 wherein $R^{13}$ is acetyl.

8. The process of claim 7 wherein the catalyst system is $Pd(OAc)_2$ and $(O-tolyl)_3P$.

9. The process of claim 8 further comprising comprises $(n-Bu)_3SnOMe$ as an enolate generator.

10. The process of claim 6 wherein $R^{13}$ is $Si(R^{14})_3$.

11. The process of claim 10 wherein $Si(R^{14})_3$ comprises $Si(Me)_3$ or $Si(t-Bu)Me_2$.

12. The process of claim 10 wherein the catalyst system comprises $PdCl_2[(p-tolyl)_3P]_2$ 13. The process of claim 12 further comprising comprises $(n-Bu)_4NF$ as an enolate generator.

14. The process of claim 5 wherein the reactant is a compound of the formula II.

15. The process of claim 14 wherein the catalyst system comprises $(O-tolyl)_3P$ and $Pd(OAc)_2$.

16. The process of claim 15 further comprising comprises NaH as an enolate generator.

17. A method for producing a compound of the formula

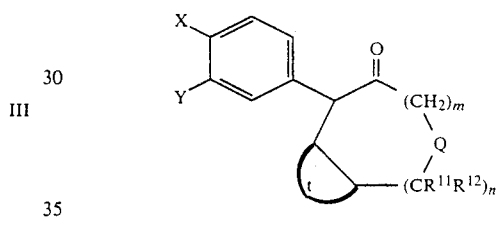

comprising reacting a compound of formula III

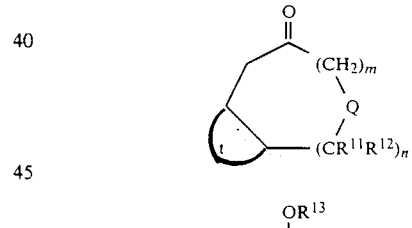

with a compound of the formula

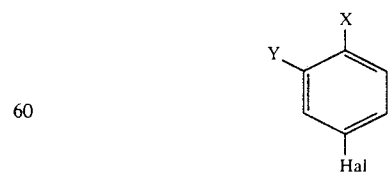

where:
ring is a fused benzene;
Q is $-CH_2-$;
m is zero;
n is 1;

$R^{11}$ and $R^{12}$ of H;
X is chlorine;
Y is methoxy; and
Hal is bromine;
and $R^{13}$ is acetyl, Si(Me)$_3$ or Si(t-Bu)Me$_2$ A. in the presence of a catalyst system comprising Pd(OAc)$_2$ and (O-tolyl)$_3$P and an enolate generator comprising
(n-Bu)$_3$SnOMe when the reactant comprises a compound of formula III where $R^{13}$ is acetyl; or B. in the presence of a catalyst system comprising PdCl$_2$[(p-tolyl)$_3$P]$_2$ and an enolate generator comprising (n-Bu)$_4$NF where the reactant is a compound of formula III where $R^{13}$ is Si(Me)$_3$ or Si(t-Bu)Me$_2$; or C. in the presence of a catalyst system comprising (O-tolyl)$_3$P and Pd(OAc)$_2$ and an enolate generator comprising NaH where the reactant is a compound of formula II.

* * * * *